United States Patent
Wagner et al.

[19]

[11] Patent Number: 5,897,319
[45] Date of Patent: Apr. 27, 1999

[54] SELF-TAPPING IMPLANT WITH HELICAL FLUTES

[75] Inventors: William R. Wagner, Escondido; Peter S. Armstrong, San Diego; Jeffrey A. Bassett, Vista, all of Calif.

[73] Assignee: Sulzer Calcitek Inc., Carlsbad, Calif.

[21] Appl. No.: 08/928,979

[22] Filed: Sep. 12, 1997

[51] Int. Cl.$^6$ .................................................. A61C 8/00
[52] U.S. Cl. .......................................... 433/174; 433/173
[58] Field of Search .................................. 433/172, 173, 433/174, 221, 225

[56] References Cited

U.S. PATENT DOCUMENTS

| | | |
|---|---|---|
| Re. 31,948 | 7/1985 | Deutsch et al. . |
| Re. 33,796 | 1/1992 | Niznick . |
| D. 273,984 | 5/1984 | Vlock . |
| D. 296,362 | 6/1988 | Branemark . |
| D. 330,767 | 11/1992 | Jorneus . |
| D. 356,868 | 3/1995 | Broberg et al. . |
| 3,067,740 | 12/1962 | Haboush . |
| 3,488,779 | 1/1970 | Christensen . |
| 3,579,831 | 5/1971 | Stevens et al. . |
| 3,732,621 | 5/1973 | Bostrom . |
| 3,846,846 | 11/1974 | Fischer . |
| 4,145,764 | 3/1979 | Suzuki et al. . |
| 4,185,383 | 1/1980 | Heimke et al. . |
| 4,187,611 | 2/1980 | Chan . |
| 4,253,833 | 3/1981 | Edelman . |
| 4,324,550 | 4/1982 | Reuther et al. . |
| 4,365,958 | 12/1982 | Vlock . |
| 4,406,623 | 9/1983 | Grafelmann et al. ............ 433/174 |
| 4,407,620 | 10/1983 | Shinjo . |
| 4,463,753 | 8/1984 | Gustillo . |
| 4,468,200 | 8/1984 | Munch . |
| 4,479,783 | 10/1984 | Weissman . |
| 4,484,570 | 11/1984 | Sutter et al. . |
| 4,495,664 | 1/1985 | Blanquaert . |
| 4,511,335 | 4/1985 | Tatum, Jr. . |
| 4,531,915 | 7/1985 | Tatum, Jr. . |
| 4,535,487 | 8/1985 | Esper et al. . |
| 4,547,157 | 10/1985 | Driskell . |
| 4,645,453 | 2/1987 | Niznick . |
| 4,713,004 | 12/1987 | Linkow et al. . |
| 4,730,969 | 3/1988 | Dohi . |
| 4,781,506 | 11/1988 | Roberts et al. . |
| 4,826,434 | 5/1989 | Krueger . |
| 4,842,518 | 6/1989 | Linkow et al. . |
| 4,851,008 | 7/1989 | Johnson . |
| 4,863,383 | 9/1989 | Grafelmann . |
| 4,871,313 | 10/1989 | Maillefer . |
| 4,878,915 | 11/1989 | Brantigan . |
| 4,932,868 | 6/1990 | Linkow et al. . |
| 5,000,686 | 3/1991 | Lazzara et al. . |
| 5,061,181 | 10/1991 | Niznick . |
| 5,064,425 | 11/1991 | Branemark et al. . |
| 5,074,790 | 12/1991 | Bauer . |
| 5,078,607 | 1/1992 | Niznick . |
| 5,087,201 | 2/1992 | Mondani et al. ................ 433/174 |

(List continued on next page.)

FOREIGN PATENT DOCUMENTS

| | | |
|---|---|---|
| 0 139 052 | 10/1983 | European Pat. Off. . |
| 0237505 | 11/1987 | European Pat. Off. . |
| 0 323 559 | 11/1988 | European Pat. Off. . |
| 30 43 336 | 11/1980 | Germany . |
| 32 41 963 | 11/1982 | Germany . |
| 85 23 007 U | 11/1985 | Germany . |
| 36 26172A1 | 2/1988 | Germany . |
| 332 486 | 2/1971 | Sweden . |
| 1 291 470 | 11/1969 | United Kingdom . |

OTHER PUBLICATIONS

3i Implant Innovations; 1995; *Speed and Control*.
Vermont Tap & Die; *TAPS Technical Information*.

*Primary Examiner*—Nicholas D. Lucchesi
*Attorney, Agent, or Firm*—Philip S. Lyren

[57] ABSTRACT

A self-tapping dental implant for implantation into bone. The implant includes multiple flutes disposed around the tapping end. Each flute has a helical configuration. During tapping, bone chips are directed upwardly and away from the tapping end.

29 Claims, 2 Drawing Sheets

U.S. PATENT DOCUMENTS

| | | |
|---|---|---|
| 5,116,225 | 5/1992 | Riera . |
| 5,167,664 | 12/1992 | Hodorek . |
| 5,194,000 | 3/1993 | Dury . |
| 5,205,746 | 4/1993 | Chanavaz . |
| 5,246,369 | 9/1993 | Poulmaire . |
| 5,269,685 | 12/1993 | Jorneus et al. . |
| 5,300,076 | 4/1994 | Leriche . |
| 5,338,197 | 8/1994 | Kwan . |
| 5,366,374 | 11/1994 | Vlassis . |
| 5,376,004 | 12/1994 | Mena . |
| 5,427,527 | 6/1995 | Niznick et al. . |
| 5,468,149 | 11/1995 | D'Alise . |
| 5,489,210 | 2/1996 | Hanosh . |
| 5,527,183 | 6/1996 | O'Brien . |
| 5,601,429 | 2/1997 | Blacklock . |
| 5,676,545 | 10/1997 | Jones .................................. 433/174 X |

5,897,319

SELF-TAPPING IMPLANT WITH HELICAL FLUTES

BACKGROUND OF THE INVENTION

Self-tapping implants are designed to be screwed into bone. During a typical surgical implantation procedure, the implantation site is exposed; and a hole is drilled into the bone. The end of the self-tapping implant is then positioned into the hole and the implant is screwed downwardly to the desired position. As the implant rotates, it simultaneously taps threads and screws into these threads.

A typical self-tapping implant has a first end for tapping threads in the bone, a second end for connecting to a prosthesis, and a threaded middle section for engaging the threads tapped in the bone. The tapping end of the implant usually consists of several grooves or flutes that extend upwardly on the sidewall of the implant along the longitudinal axis of the implant. Each flute includes a cutting edge that scrapes off bone as the implant is rotated into the hole. The cutting edges form threads along the bone for engaging the threaded section of the implant.

Present self-tapping implants offer many advantages over non-tapping implants. First, a separate bone tapping tool is not required since the implant itself taps the bone. Second, the overall time to perform the surgical implantation procedure is reduced since the bone does not first have to be separately tapped before the implant is inserted into the hole. As another advantage, self-tapping implants generally have a more intimate contact with the surrounding bone than non-tapping implants.

In spite of the foregoing advantages, present self-tapping implants also possess numerous disadvantages. For example, irregularities or defects may exist on the bone around the entrance of the hole at the implantation site. These irregularities may occur naturally or as a result of the surgical procedure, and these irregularities further may inhibit bone integration with the implant. Prior self-tapping implant designs do not remedy these irregularites.

As another disadvantage, bone chips tend to accumulate at the cutting edge while the implant is being tapped into the bone. These bone chips decrease the effectiveness of the cutting edge and further increase the insertion torque required to insert the implant. The tapping end of the implant should have a geometry to cut bone chips and then direct these chips away from the cutting edge.

As yet another disadvantage, some prior self-tapping implants push bone chips downwardly or away from the threads on the implant. If these bone chips were directed to tightly pack around the threads, then the implant would be more stable in the bone.

SUMMARY OF THE INVENTION

The present invention is directed toward a self-tapping implant that screws into a hole in bone. The implant comprises a tapping end for tapping threads into bone, a coronal end for connecting to a prosthesis, and a threaded middle section for engaging the threads tapped into the bone. In the preferred embodiment, the tapping end has three separate helical flutes that begin at the apical end of the implant and spiral toward the coronal end. The configuration of the tapping end provides numerous advantages.

One important advantage over the prior art is that the cutting edge and configuration of the flutes push bone chips upwardly toward the entrance of the hole at the implantation site. Bone chips exit the hole and are deposited along the surface of the bone adjacent the entrance. These chips fill in irregularities or defects around the hole and, in turn, provide a more even and smooth surface.

As another advantage, the configuration of the flutes pushes bone chips away from the cutting edge. In particular, bone chips are pushed upwardly along the curvature of the flute.

As a further advantage, the present implant is more stable and secure once it is implanted in the bone. The helical flutes move bone chips so they tightly pack around the threaded middle section and second end.

The invention, accordingly, comprises the apparatus possessing the construction, combination of elements, and arrangement of parts which are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENTS

Figure 1:
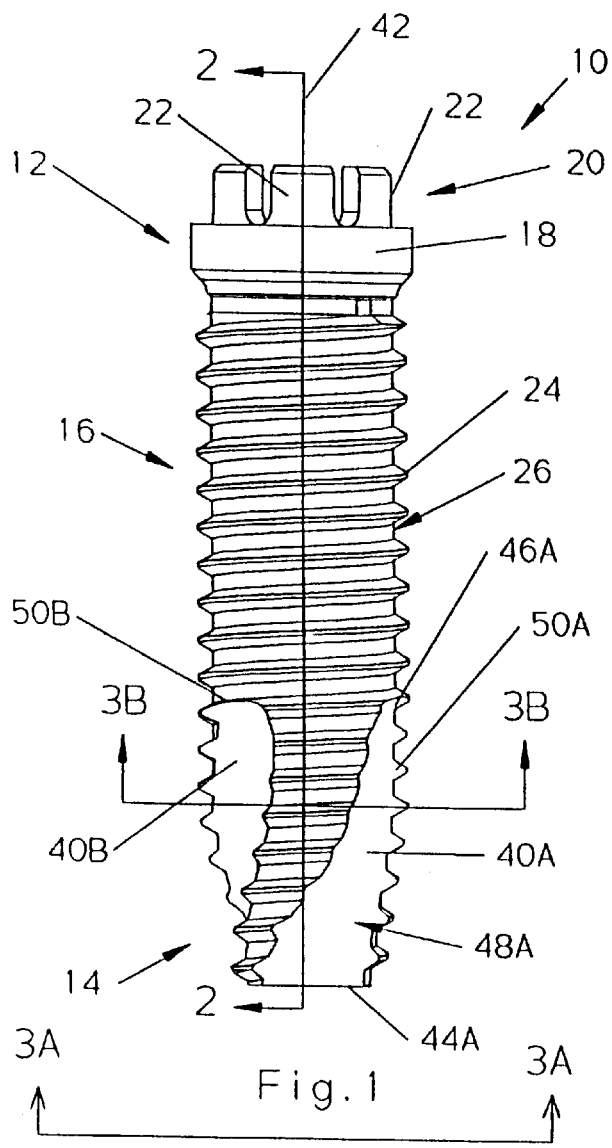
FIG. 1 is an elevation view of a self-tapping implant according to the invention.

FIG. 1 shows a self-tapping implant at 10. Implant 10 has a generally elongated cylindrical configuration and includes a coronal end 12, a tapping end 14 oppositely disposed from the coronal end, and a threaded middle section 16 disposed between the two ends. The implant may be any one of various dental implants known to those skilled in the art and designed to be implanted into bone. For illustration purposes, implant 10 is shown as a dental implant, known as SPLINE TWIST™ manufactured by Sulzer Calcitek of Carlsbad, Calif. The implant preferably is formed from a titanium alloy and may have any one of various surface coatings or surface textures, such as an as-machined surface or microtextured surface. Texturing of the threaded surface can be accomplished by a variety of processes known to those skilled in the art, such as grit-blasting with an abrasive medium or etching with a strong acid.

End 12 includes an interface ring 18. A prosthetic interface 20 extends upwardly from interface ring 18. The prosthetic interface includes a plurality of splines or tines 22 for engaging a dental prosthesis or part of a prosthetic attachment system (not shown). These splines are taught in U.S. Pat. No. 5,449,291 entitled "Dental Implant Assembly Having Tactile Feedback" issued to Lueschen et al.; this patent is fully incorporated herein by reference.

Threaded middle section 16 is disposed between end 12 and end 14. This section includes threads 24 that helically extend around a cylindrical body portion 26 of implant 10. Threads 24 may have any one of various configurations known to those skilled in the art.

Figure 2:
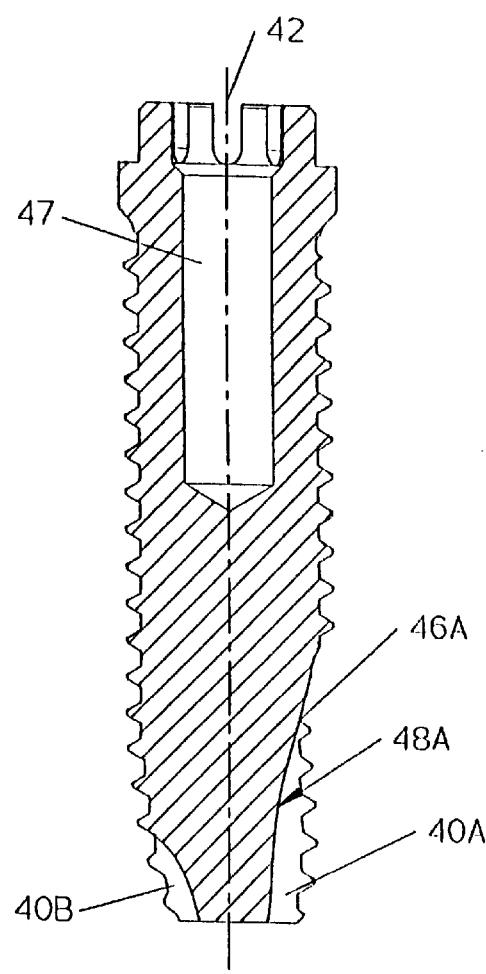
FIG. 2 is a cross-section of the implant of FIG. 1.

Reference is now simultaneously made to FIGS. 1–3. End 14 performs the tapping function of implant 10. In the preferred embodiment, this end includes three separate flute sections shown as 40A, 40B, and 40C, respectively. Flutes 40A, 40B, and 40C extend upwardly along a longitudinal axis 42 that centrally extends through implant 10. These flutes are disposed around body portion 26 and are symmetrically spaced. Further, each flute is configured similarly.

The details of flute 40A are fully shown in FIG. 1. Flute 40A has a helical configuration that spirals in a clockwise direction about longitudinal axis 42. The flute has a continuous curvature that extends from a tip 44A of tapping end 14 to a termination point 46A. Tip 44A perforates the bottom of tapping end 14. The overall length of the flutes may vary. The flutes, for example, may extend from the apical end of the implant completely to the coronal end of the implant. Preferably, the flutes do not extend completely to the coronal end. FIG. 2 shows the preferred embodiment in which the flutes extend to a point below an internal cavity 47 that extends from the coronal end for receiving a screw (not shown). In FIG. 1, the length of flute 40A extends approximately one third the entire length of the implant.

The flutes shown in FIGS. 1 and 2 become submerged below the surface of the bone before the implant is fully seated. Continued insertion of the implant into the implantation site after the flutes become submerged further packs bone chips around the implant. The bone chips packed around the implant in this manner increase the stability and security of the implant in the bone.

Figure 3A:
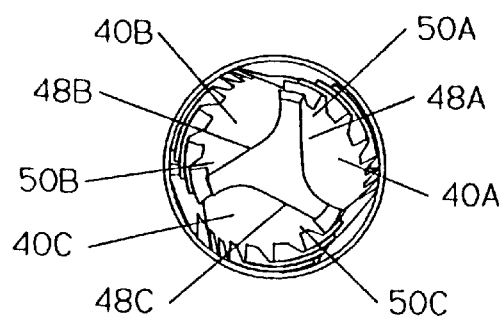
FIG. 3A is an enlarged end view of the implant of FIG. 1 taken along the line 3A—3A.

As best seen in FIGS. 1 and 3A, flutes 40A, 40B, and 40C form a cavity 48A, 48B, and 48C that extends into body 26. Each cavity has a curved configuration with a somewhat concave shape. The configuration of the cavity, however, changes as the flute transitions from the tip of tapping end 14 to the termination point.

Figure 3B:
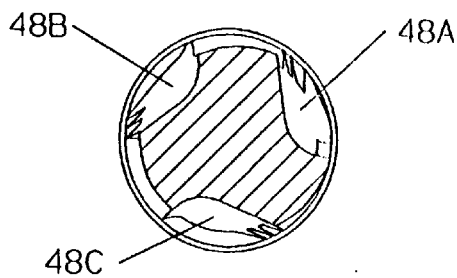
FIG. 3B is an enlarged cross-section of the implant of FIG. 1 taken along the line 3B—3B.

Looking to FIGS. 3A and 3B, the cavities have a depth that extends into body 26 along longitudinal axis 42. Preferably, this depth varies over the length of the flute. Looking at flute 40A for example, the depth of cavity 48A is greatest at tip 44A of tapping end 14. This depth gradually diminishes or tapers as flute 40A transitions to termination point 46A.

The cavities also have a width that varies over the length of the flute. Again looking to flute 40A, the width of cavity 48A is greatest at tip 44A of tapping end 14. This width gradually diminishes or tapers as flute 40A transitions to termination point 46A.

The tapering of the width and the depth are particularly advantageous since more threaded surface area exists between adjacent flutes as the flutes extend upwardly from the tip to the termination point. As such, the stability of the implant is enhanced.

Each flute 40A, 40B, and 40C includes a primary cutting edge or surface 50A, 50B, and 50C, respectively. This cutting edge extends along one side of the flute. FIG. 2 shows a generally smooth transition from the cutting edge to the cavity. Preferably, the cavity does not have any abrupt corners or edges and hence is smooth. The smooth transition from the cutting edge to the cavity and additionally within the cavity itself helps to direct a smooth flow of bone chips away from the cutting edge and along the cavity. In turn, the insertion torque required to insert the implant is reduced.

During tapping, a hole is first drilled into the bone of the implantation site. Then, end 14 is inserted into the implantation site and implant 10 is rotated clockwise. The cutting edge cuts and scrapes bone chips from surrounding bone as the implant is rotated. These bone chips are pushed away from the cutting edge into the adjacent flute. The movement of these bone chips away from the cutting edge prevents unwanted clogging or accumulation of chips at the cutting edge.

Figure 4:
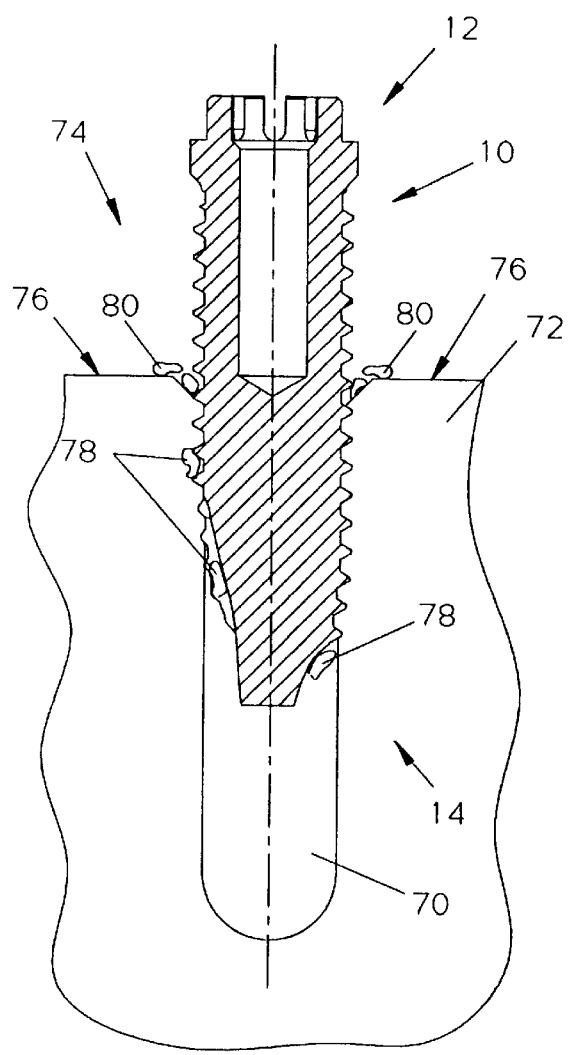
FIG. 4 is a cross-section of the implant of FIG. 1 partially tapped into bone.

One important advantage of the present invention is that bone chips move upwardly away from the tapping end of the implant. FIG. 4 shows a cross-section of implant 10 being tapped into a hole 70 in bone 72 at an implantation site 74. The surface of the bone at the implantation site may be a rough, uneven, or otherwise defective shown at 76. These surface conditions may occur naturally or may be formed during the implantation procedure. As the implant is tapped downwardly into hole 70, bone chips 78 are directed upwardly from tapping end 14 toward coronal end 12. Some of these bone chips 80 exit hole 70 and deposit at the implantation site adjacent coronal end 12.

Figure 5:
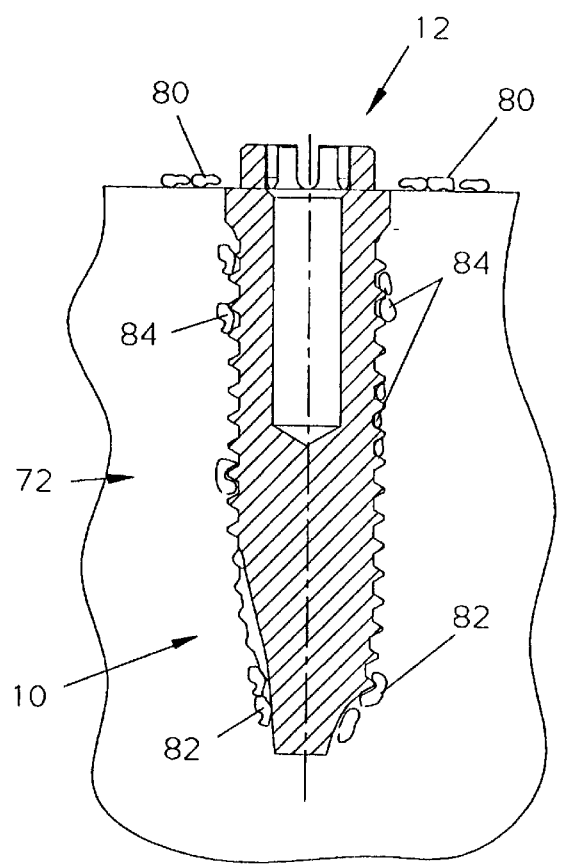
FIG. 5 is a cross-section of the implant of FIG. 1 fully tapped into bone.

FIG. 5 shows a cross-section of implant 10 after being tapped into hole 70. Bone chips 80 have moved into the rough surface conditions (FIG. 4) adjacent coronal end 12. The surface adjacent the coronal end is now more smooth and contains less defects. FIG. 5 also reveals that bone chips 82 have been directed around the exterior of the tapping end of the implant. Other bone chips 84 exist in the threads located between the termination point and the coronal end. Bone chips 82 and 84 pack tightly around the implant and increase the overall stability of the implant.

FIGS. 1–3 show an implant that has three different flute sections 40A–40C. The number of flutes may vary; three flutes are shown to illustrate the preferred embodiment. An implant having a larger diameter, for example, may utilize four or more separate flute sections around the tapping end. Alternatively, an implant with one or two flutes about the tapping end is within the scope of this invention. Further, FIG. 1 shows flutes that spiral in a clockwise direction about the implant. These flutes may also be configured to spiral in a counter clockwise direction about the implant.

Since certain changes may be made in the above-described method and apparatus without departing from the scope of the invention herein involved, all matter contained in the description or shown in the accompanying drawings shall be interpreted as illustrative and not in a limiting sense.

The invention claimed is:

1. A self-tapping dental implant for anchoring in bone, comprising:

a generally cylindrical shaped body having a middle portion with a threaded section and an end portion with a tapping section, wherein said tapping section includes two separate helically shaped flutes, wherein each flute includes a cutting surface that extends substantially along one edge thereof.

2. The dental implant of claim 1 in which:

said cutting surfaces remove bone chips from said bone; and said flutes direct said bone chips away from said cutting surface and upwardly toward said middle portion.

3. The dental implant of claim 1 in which;

said flutes extend from said end portion to said middle portion;

said flutes have a concave configuration; and said flutes have a depth that gradually tapers from said end portion to said middle portion such that said flutes are deeper at said end portion than at said middle portion.

4. The dental implant of claim 1 in which:

said flutes extend from said end portion to said middle portion;

said flutes have a concave configuration; and said flutes have a width that gradually tapers from said end portion to said middle portion such that said flutes are wider at said end portion then at said middle portion.

5. The dental implant of claim 1 in which:

said body further includes a coronal end adjacent said middle portion and oppositely disposed from said end portion;

said cutting surfaces remover bone chips from said bone; and said flutes direct bone chips away from said end portion and toward said coronal end.

6. The dental implant of claim 5 in which a portion of said bone chips exit said flutes and deposit at said middle portion.

7. The dental implant of claim 5 in which a portion of said bone chips exit said flutes and deposit at said coronal end.

8. The dental implant of claim 5 in which:

said body has a first length;

said flutes have a second length that is less than one half said first length; and said flutes are submerged within said bone before said implant is fully seated within said bone.

9. A self-tapping dental implant for anchoring in bone, comprising:

a body having a middle section with externally disposed threads, a coronal section adjacent said middle section, and a tapping section adjacent said middle section and oppositely disposed from said coronal section;

a longitudinal axis that extends through said body from said coronal section to said tapping section; and two separate flutes that penetrate said body at said tapping section, wherein said flutes spiral at least partially around said longitudinal axis.

10. The implant of claim 9 in which:

each end of said flutes includes a cutting edge that removes bone chips while said implant is being tapped into said bone; and said flutes direct a first portion of said bone chips upwardly to said middle section.

11. The implant of claim 10 in which said flutes direct a second portion of said bone chips upwardly to said coronal section.

12. The implant of claim 9 in which said body has a machined titanium or microtextured titanium surface.

13. A method for anchoring a dental implant into bone, comprising the steps of:

drilling a hole into said bone;

providing an implant having a coronal section, a threaded middle section adjacent said coronal section, and a tapping section oppositely disposed from said coronal section and having at least one helical flute with a cutting edge;

positioning said tapping section in said hole;

rotating said implant into said hole;

removing bone chips with said cutting edge; and directing said bone chips upwardly and away from said tapping section to said middle section and said coronal section and out of said flute.

14. The method of claim 13 further comprising the step of directing a portion of said bone chips out of said hole.

15. The method of claim 13 further comprising the step of depositing said portion of bone chips adjacent said coronal end.

16. The method of claim 13 further comprising the step of directing a portion of said bone chips between said threads at said middle section.

17. A self-tapping dental implant for anchoring in bone, comprising:

a generally cylindrical shaped body having a middle portion with a threaded section and an end portion with a tapping section, wherein said tapping section includes a cutting surface formed along one edge of a helically shaped flute;

said flute extends from said end portion to said middle portion;

said flute has a concave configuration; and said flute has a depth that gradually tapers from said end portion to said middle portion such that said flute is deeper at said end portion than at said middle portion.

18. A self-tapping dental implant for anchoring in bone, comprising:

a generally cylindrical shaped body having a middle portion with a threaded section and an end portion with a tapping section, wherein said tapping section includes a cutting surface formed along one edge of a helically shaped flute;

said flute extends from said end portion to said middle portion;

said flute has a concave configuration; and said flute has a width that gradually tapers from said end portion to said middle portion such that said flute is wider at said end portion then at said middle portion.

19. A self-tapping dental implant for anchoring in bone, comprising.

a body having a middle section with externally disposed threads, a coronal section adjacent said middle section, and a tapping section adjacent said middle section and oppositely disposed from said coronal section;

a longitudinal axis that extends through said body from said coronal section to said tapping section;

two separate flutes on said body at said tapping section, wherein said flutes spiral at least partially around said longitudinal axis;

said flutes extend from said tapping section to a termination point at said middle section;

a cutting edge located partially along said flutes removes bone chips while said implant is being screwed into said bone; and said cutting edge pushes bone chips out of said flutes through said termination point.

20. A self-tapping dental implant for anchoring in bone, comprising:

a body having a middle section with externally disposed threads, a coronal section adjacent said middle section, and a tapping section adjacent said middle section and oppositely disposed from said coronal section;

a longitudinal axis that extends through said body from said coronal section to said tapping section; and three separate flutes on said body at said tapping section, wherein said flutes spiral at least partially around said longitudinal axis and said flutes are symmetrically positioned around said longitudinal axis.

21. The implant of claim 20 in which:

each of said flutes includes a cutting edge that removes bone chips while said implant is being tapped into said bone; and said flutes direct a first portion of said bone chips upwardly to said middle section.

22. The implant of claim 21 in which said flutes direct a second portion of said bone chips upwardly to said coronal section.

23. The implant of claim 20 in which:

said flutes extend from said tapping section to a termination point at said middle section;

a cutting edge located partially along said flutes removes bone chips while said implant is being screwed into said bone; and said cutting edge pushes bone chips out of said flutes through said termination point.

24. The implant of claim 20 in which:

said flutes extend from a start point at said tapping section to a termination point at said middle section; and said flutes have a greater depth at said start point then at said termination point.

25. The implant of claim 24 which said flutes have a greater width at said start point then at said termination point.

26. The implant of claim 20 in which said body has a machined titanium or microtextured titanium surface.

27. The implant of claim 20 in which said flutes include a cutting edge that removes bone chips from said bone; and said flute directs said bone chips away from said cutting edge and upwardly toward said middle portion.

28. A self-tapping dental implant for anchoring in bone, comprising:

a body having a middle section with externally disposed threads, a coronal section adjacent said middle section, and a tapping section adjacent said middle section and oppositely disposed from said coronal section;

a longitudinal axis that extends through said body from said coronal section to said tapping section;

two separate flutes on said body at said tapping section, wherein said flutes spiral at least partially around said longitudinal axis;

said flutes extend from a start point at said tapping section to a termination point at said middle section; and said flutes have a greater depth at said start point then at said termination point.

29. The implant of claim 28 in which said flutes have a greater width at said start point then at said termination point.

\* \* \* \* \*